United States Patent [19]

Sudderth

[11] Patent Number: 4,747,776
[45] Date of Patent: May 31, 1988

[54] ARTIFICIAL TEETH AND CARDING SYSTEM AND METHOD

[76] Inventor: Franklin T. Sudderth, 110 Ridgeland Dr., Greenville, S.C. 29601

[21] Appl. No.: 911,164

[22] Filed: Sep. 24, 1986

[51] Int. Cl.⁴ ............................................. A61C 19/10
[52] U.S. Cl. ....................................................... 433/26
[58] Field of Search ................ 433/26; 24/67.9, 67.11, 24/294, 297

[56] References Cited

U.S. PATENT DOCUMENTS

| | | | |
|---|---|---|---|
| 2,987,841 | 6/1961 | Phillips | 24/67.9 |
| 3,521,357 | 7/1970 | Berglund et al. | 433/26 |
| 4,306,860 | 12/1981 | Janssen et al. | 433/26 |

*Primary Examiner*—Robert Peshock
*Attorney, Agent, or Firm*—Cort Flint

[57] ABSTRACT

A carding system and method for artificial teeth is disclosed wherein artificial teeth (A, D, C, E, and F) may be carded on a tooth card (B). The tooth card (B) comprises an elongated extruded plastic strip (10) having a vertical flange (14) and a split retainer tube (12). The artificial teeth are provided with various means of retaining the teeth on retainer tube (12) such as retainer slots (26), retainer bars (70 and 78). Retainer tube (12) includes prong-like edges (18 and 20) defined by slit (16) which compress together to enable fitting of teeth with retention slots (26) onto retainer tube in a snap action. Retainer tube (12) likewise retains teeth with retainer bars by allowing the shank (74, 80) to fit between the prong-like edges with enlarged head (76, 82) preventing outward movement of teeth. Conventional pins (32) of artificial teeth may also be retained by retainer tube. In accordance with the method, tooth cards (B) are automatically produced in a continuous strip (46) by an extrusion molding process and are simultaneously imprinted with identification indicia (35a, 35b, 36, 38, and 40). The extruded strip is then cut into individual tooth cards and artificial teeth which have been molded and retained by a molding cavity (54) are automatically loaded onto an aligned tooth card (B) whereby as set of teeth is carded having a predetermined description and identification the tooth card.

26 Claims, 3 Drawing Sheets

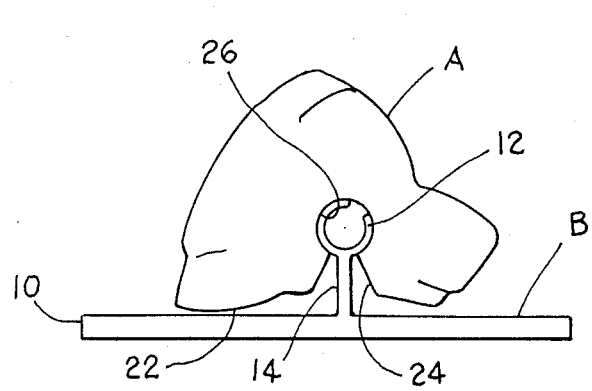
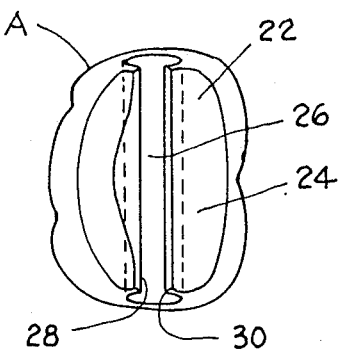
Fig. 1.
Fig. 2.
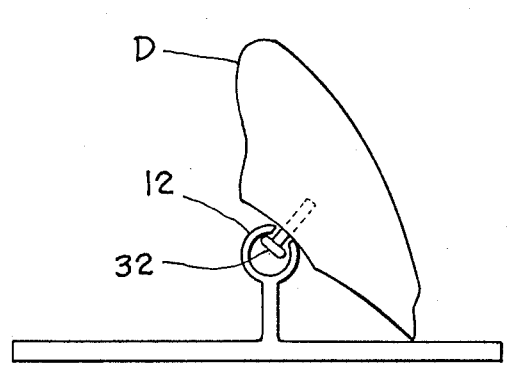
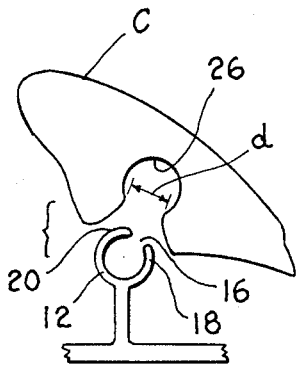
Fig. 3.
Fig. 3A.
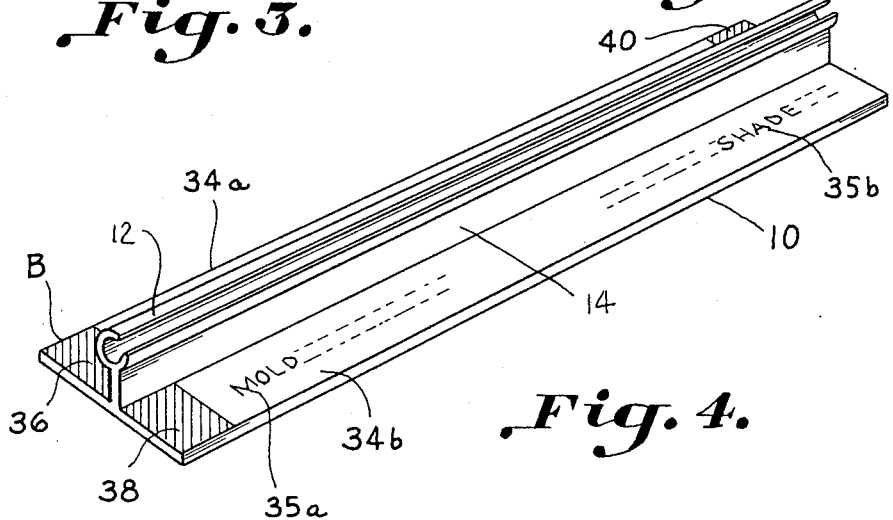
Fig. 4.

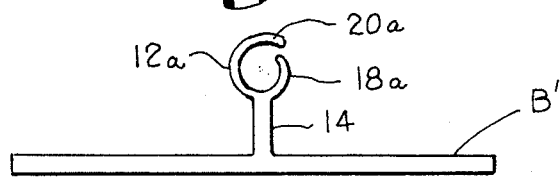
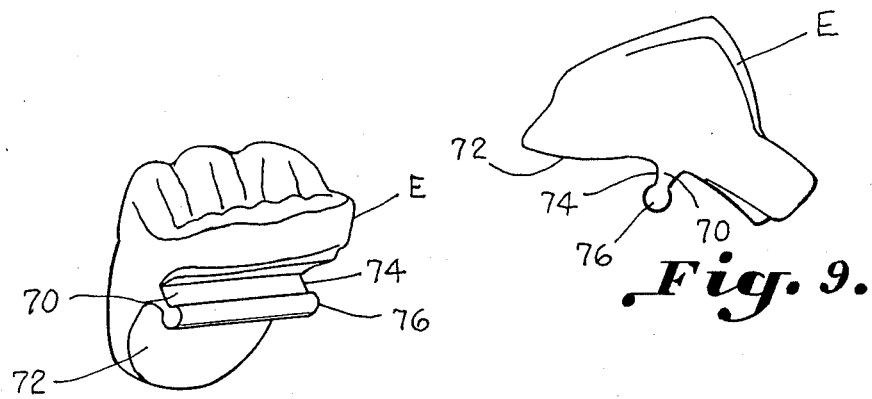
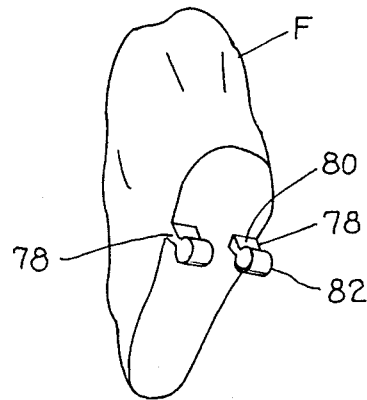
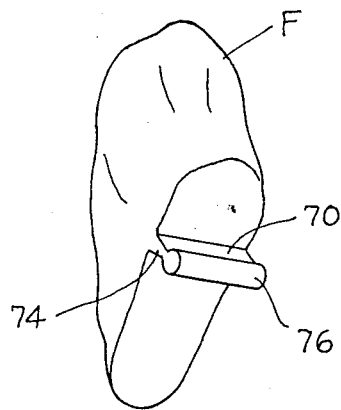

ARTIFICIAL TEETH AND CARDING SYSTEM AND METHOD

BACKGROUND OF THE INVENTION

The invention relates to the manufacture and carding of artificial teeth for dentures. In the manufacture of dentures, it is necessary to select the size and shape of artificial teeth in a compatible manner with the facial characteristics of the patient. In the manufacture of artificial teeth, the artificial teeth are identified by mold shade, and type of material they are made from. Typically the manufactured teeth are placed in a set on a tooth holder commonly called a card and are identified by the mold and shade of the teeth. The tooth card may hold a set of related artificial teeth like a set of anterior or posterior, upper or lower teeth. A dental laboratory orders and receives a set of artificial teeth on the card. The carded teeth may be used to display the teeth to the patient and the dental lab technician works from the carded teeth to fashion and make the dentures in accordance with the prescription.

Various ways of retaining the artificial teeth on the card have been known. It has been quite common, in connection with tooth cards, to provide either a strip or panel of wax, preferably of a somewhat tacky nature, to which the artificial teeth are affixed by various means, including the pins normally projecting from the pin-shelf of anterior porcelain artificial teeth, for example. Such pins are embedded in the wax of the holder and it is convenient to handle artificial teeth of this type in related sets such, for example, as six anterior teeth respectively comprising left and right canine teeth at opposite ends of the set, left and right lateral teeth, inward from the latter, and left and right central teeth in the center of the set of teeth. Usually, a set of such upper anteriors is mounted on one card and a corresponding set of lower anteriors will be mounted on a separate card, in accordance with customary practice.

Posterior artificial teeth, such as the first and second molars, and first and second bicuspids, including both left and right of each, will be mounted on a tooth card in sets of eight, respectively for upper and lower dentures.

When these sets of related teeth are prepared upon such tooth cards by a manufacturer, the assembled teeth in each set usually have either identical or closely related shades, and the proportion, shape and size (mold) are related so that, with the other characteristics, they are rendered as close as possible in appearance to natural teeth which they are to replace.

After the dentist makes an impression of the patient's mouth and the teeth have been selected, the impression and prescription are sent to a dental laboratory. The dental laboratory then makes up a model of the patient's mouth according to the impression and attaches the prescribed teeth to the model by means of a wax base plate. The resulting unit is called a "try in" which unit is sent to the dentist who tries the unit in the patient's mouth. Upon satisfactory approval, the "try in" unit is then sent back to the dental laboratory. At the dental laboratory, a plaster mold is made of the "try in" unit. The artificial teeth stay in the plaster mold and the wax base plate is boiled out. A suitable plastic such as acrylic is then filled in the space that the wax plate previously occupied. Next, the acrylic material is processed by heat, then it is broken out of the plaster, leaving the denture. The same process is followed for both upper and lower dentures.

In affixing the artificial teeth to the acrylic material, it is necessary to provide a means of either mechanically or chemically connecting the two together. Heretofore, in the case of porcelain anteriors, the teeth are provided with pins having pinheads which are embedded in the acrylic material. The porcelain posteriors are typically provided with a diatoric hole. Various plastic materials and compositions have also been utilized in the manufacture of artificial teeth such as acrylic and acrylic compositions. In the case of plastic artificial teeth, the teeth are typically provided only with a mating surface which is adhered to the acrylic material of the denture base by chemical bonding. No mechanical retention is provided.

In securing teeth to a tooth card, porcelain teeth are typically secured on a card with wax material which retains the teeth. In repairing a set of dentures made of porcelain teeth, the replacement teeth have wax material left on the base of the teeth. The wax material creates a problem in adhering to the tools and hands of the technician. The wax material comes in various colors and is difficult to completely remove from the teeth. The colored wax material often shows up on the "try in" model which is not a pleasing appearance to the patient resulting in a not entirely satisfactory display or process. Considerable time and effort is required to completely remove the wax material from the teeth. This may be done by cleaning the material off with a knife or by enflaming and then wiping the teeth clean with a cloth. In either case, due to the time and effort involved, this is typically not carried out resulting in the above mentioned problems. U.S. Pat. No. 3,018,884 shows a conventional method for carding teeth by means of a wax card.

Another problem with the wax card is that the plastic and porcelain teeth are not always retained well by the wax material causing the teeth to fall off of the card presenting a problem of loose teeth and difficult identification. This is particularly true in extreme hot summer and cold winter weather when the wax becomes extremely hot and extremely cold.

Plastic, i.e. acrylic, teeth are also typically carded on wax cards. Due to the absence of any holes or pins on the plastic teeth, the problem of cleaning the wax material from the plastic teeth is not quite as accute. However, because there is no retention by pins or holes the plastic teeth are not as securely retained on the wax cards and are more likely to become loose.

Various carding devices have been proposed for artificial teeth by which teeth may be mechanically retained on the card such as shown on U.S. Pat. Nos. 1,248,030; 675,044; 691,551; 2,111,095; and 1,573,858. The above mentioned carding devices have not been entirely satisfactory, partially for the reason that the corresponding retention part of the tooth has required openings to be formed in the teeth which leave thin, weakened tooth areas susceptible to breakage and are not entirely satisfactory. Further, the retention often requires a tedious manual maneuvering of the artificial teeth on the mechanical retention part in order to take the teeth on and off. The artificial teeth may be easily dislodged from some of the mechanical retention features.

U.S. Pat. No. 2,302,376, and 2,334,214 disclose carding devices for artificial teeth in which anterior teeth are placed by wax retention on a holder to be placed in a patient's mouth for determination of a satisfactory appearance.

In the anchoring of plastic teeth to the denture base, if a good chemical bond is had between the acrylic denture base and the plastic teeth, then problems are normally not encountered. However, due to the lack of any mechanical innerlocking features, plastic teeth may easily dislodge from the denture base if a good chemical bond is not had.

Artificial porcelain teeth have been provided with different openings, holes, and other mechanical features to anchor them to the denture base material. For example, artificial teeth are shown in U.S. Pat. No. 200,284, disclosing very early the formation of openings in artificial teeth, which openings are used to retain the teeth on the denture base material. However, in this early stage of the art, the compatibility of the teeth for purposes of carding the teeth was not a consideration. Teeth of this type may be considerably more difficult to card.

U.S. Pat. No. 2,600,496 discloses anchorage for plastic artificial teeth in which teeth are disclosed with metal embedded in the teeth for purposes of anchoring the teeth. These type teeth are considerably more complicated and expensive to manufacture than the present day porcelain and plastic, and are more difficult to card.

U.S. Pat. No. 411,272 discloses artificial teeth embedded in a denture base by means of spring clips. This very early method of securing teeth was particularly for securing teeth to vulcanite material which is a rubbery base material having particular retention problems.

U.S. Pat. No. 691,550 discloses anchoring teeth in a wax card by using a wire loop which extends into the diatoric hole. This type anchor is very susceptible to becoming loose. U.S. Pat. No. 675,044 proposes mounting of diatoric teeth by wiring them on a rigid strip.

Accordingly, an object of the invention is to provide an improved carding system and method for carding and manufacturing of artificial teeth and dentures in which artificial teeth are retained without wax.

Another object of the invention is to provide a carding system for artificial teeth wherein artificial teeth may be manufactured and carded in a systematic automated way including extrusion, printing, coding, cutting individual card lengths.

Another object of the invention is to provide a card for artificial teeth that can be utilized in an automated manner so that the artificial teeth on a card can be automatically loaded on a card as the artificial teeth are molded.

Another object of the invention is to provide a card for carding artificial teeth that uses less material to manufacture, is reusable, and with a universal product code printed on the base of the card, the card may be used for automated inventory, invoicing, ordering, and reordering by automatic reading of the universal product code.

Another object of the invention is to provide artificial teeth having a design for both porcelain and acrylic materials that is compatible with the carding system of the present invention and also gives equal or superior retention in the denture base material, which is particularly a problem with plastic teeth.

Another object of the invention is to provide a card without wax that will retain present porcelain anterior teeth with pins.

Another object of the invention is to provide a card and carding system for artificial teeth that securely retains the teeth so that only minimal packing material is required for shipping, if at all.

Still another object of the invention is to provide a card and carding system for artificial teeth that will hold the teeth in relative proximity so the card may be manually picked up with the teeth on the card and placed alongside the edentelous area to determine if the teeth are the correct length and size to suit the edentelous area.

Yet another object of the invention is to provide a card and artificial teeth wherein the carded teeth may be individually removed and reattached to the card without disturbing the remaining teeth on the card.

SUMMARY OF THE INVENTION

The above objectives are accomplished according to the present invention by providing a tooth card having a base and a split retainer tube carried on a flange extending up from the base. The retention tube includes a narrow slit extending along its length. Artificial teeth made in accordance with the invention include, in the case of plastic teeth, such as acrylic, a retainer slot in the posterior and anterior teeth in which the retention tube may be inserted by a spring or sliding action. A pair of prongs are created by the slit formed in the retention tube, by which the retention tube may be compressed to allow the retention ring to enter and snap into the retention slot of the teeth. In the case of porcelain teeth provided with pins, the stem of the anchor pin of the tooth may be slidably received the slit of the split retainer tube for retention on the card. Likewise, plastic teeth may be molded with a retainer bar, rather than a slot, which fits in the slit of the retainer tube. Advantageously, the card itself may be extruded in an automatic manner and with the universal product code printed on an underneath portion of the card and the mold and shade printed on the top of the base of the card. Since the teeth may be carded in a longitudinal sliding motion along the retention

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein:

FIG. 1 illustrates an artificial posterior tooth constructed for plastic or porcelain and carded in accordance with the present invention;

FIG. 2 is a bottom plan view of the posterior tooth of FIG. 1;

FIG. 3 is a side elevation of a porcelion anterior tooth carded in accordance with the present invention;

FIG. 3A is a side view of a plastic anterior tooth constructed and carded in accordance with the invention illustrated prior to being fastened to the split retention tube of the card;

FIG. 4 is a perspective view of a tooth card or card strip constructed in accordance with the present invention;

FIG. 5 is a perspective view illustrating the automatic manufacture, printing, coding, cutting of tooth cards and method in accordance with the present invention;

FIG. 8 is an alternated embodiment of a tooth card constructed in accordance with the present invention;

FIG. 9 is an elevation of an alternate embodiment of an artificial posterior tooth according to the invention;

FIG. 10 is a rear perspective view of a tooth back illustration alternate anchoring of an artificial tooth according to the invention;

FIG. 11 is a rear perspective view of an anterior tooth illustrating alternate anchoring of an artificial tooth according to the invention; and FIG. 12 is a rear perspective view of an anterior tooth illustrating alternate anchoring of an artificial tooth according to the invention.

DESCRIPTION OF A PREFERRED EMBODIMENT

Figure 5:
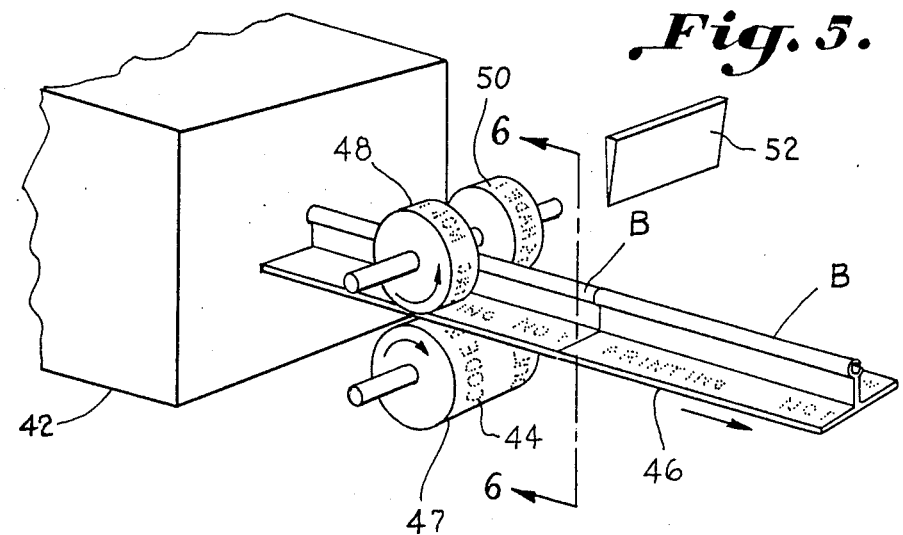
FIG. 5 is a perspective view illustrating the automatic manufacture, printing, coding, cutting of tooth

Referring in more detail to the drawings, FIG. 1 illustrates a posterior tooth which may be constructed from a plastic or porcelain material in accordance with the present invention. The tooth is designated as A. There is a tooth card or carding strip B having a base 10 and a split retainer tube 12 extending longitudinally across the base and attached thereto by means of a vertically extending flange 14. As can best be seen in FIGS. 3 and 3a, the split retainer tube of card B includes a narrow slit 16 extending along its length. The retainer tube 12 terminates at pronglike edges 18 and 20 which are created by slit 16. These edges flex towards each other to facilitate retention of artificial teeth thereon. This can be visualized by viewing retainer tube 12 in cross section (FIG. 3A), wherein a split ring is apparent which includes a pair of flexing opposing prongs 18 and 20. Prongs 18 and 20 may be moved towards each other closing the narrow slit 16 to allow for retention of the teeth on the card either by sliding onto or insertion over the retainer tube.

In the case of posterior teeth A, a naturally shaped tooth back 22 is provided having an inwardly tapering opening 24. Opening 24 tapers inwardly to a retainer slot 26 formed across tooth A open at each end, as can best be seen in FIG. 2. Retainer slot 26 extends along the mesial and distal dimensions of the posterior teeth. Opposing retention ledges are provided at 28 and 30 defined by the intersection of retainer slot 26 and the tapering surface 24.

The dimension "d" between opposing ledges 28 and 30 is defined so that the prongs 20 and 18 may suitably come together for insertion of the split tube into retainer slot 26. Dimension "d" should be that dimension which permits insertion but at the same time secures the tooth on retainer tube 12. It is also necessary that slot 16 not be made too wide so that a conventional metal pin 32 of an anterior porcelain tooth C illustrated in FIG. 3 can be may slidably fit for retention and longitudinal movement along retainer tube 12. Alternately, a card B and split tube 12a may be formed so that prong-like edges 20a and 18a over lap each other (FIG. 8) allowing retainer tube 12 to assume a smaller diametrical cross section compressed facilitating easy retainer slot engagement. In this manner, dimension "d" may be made less. This may be necessary where a smaller cross section slot 26 is desired so that areas of the teeth are not overly weakened. For example, anterior teeth are highly susceptible to breakage thru weakening hole structure. At the same time, overlapping prongs 20 and 18 may still accommodate retention pin 32 of a porcelain anterior tooth.

Referring now in more detail to tooth card B and automatic method according to the invention. Base 10 may include first and second opposing upper base surfaces 34a and 34b on either side of vertical flange 14. On one upper base surface, for example 34b, the mold identification and shade upper side of the base at 36, 38, and 40. These areas may be imprinted with a prescribed color to indicate the model or type of teeth. For example, a first code section 36, 38 may indicate model or type of teeth (i.e. material). A second code section 40 at a second, opposing end of the card, may indicate upper or lower denture teeth. If the color code band 40 is shown as depicted in FIG. 4 on the first base surface 34a this would indicate that the teeth are upper denture teeth. If color band 40 is on the second base surface 34b of base 10, this would indicate that the teeth are lower denture base teeth.

Figure 6:
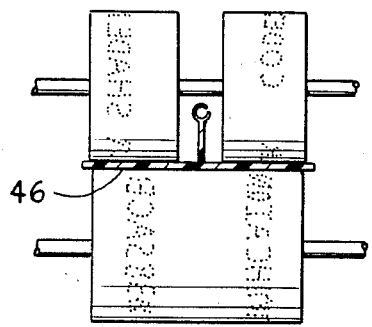
FIG. 6 is a sectional view taken along line 6—6 of FIG. 5.

As can best be seen in FIG. 5, the printing of the carding strip may be done automatically as the carding strip leaves an extruding machine designated schematically as 42. It is to be understood, of course, that while it is preferred that the carding strip be extruded from a plastic material, other materials or construction may be utilized if found suitable. Plastic material, of course, is particularly suitable so that the prongs 20 and 18 of retainer tube 12 properly compress for engagement into retaining slots and for removal. While in the printing stage of the automatic process according to the invention, a universal product code 44 may be imprinted onto an underneath side 46 of base 10 as can best be seen in FIGS. 5 and 6. For this purpose a lower printing wheel 47 may be provided to imprint the universal product code. Universal product code 44 may be of the machine readable type. In this way, inventory control and reordering may be simplified. The empty tooth card B can be read by a machine or automatically input inventory control for reorder of that type teeth. A printing wheel 48 prints color band 38, mold identification and shade identification all appearing on upper surface 34b of base 10. Printing wheel 50 prints color band 36, manufacture name, and color band 40 on side 34a of the upper surface of base 10. If color band 40 is to be printed on side 34b of base 10, then such will be provided on printing wheel 48 instead of printing wheel 50. Any suitable cutting device may be utilized at 52 for cutting the carding strips into individual strips as shown in FIG. 5.

Figure 7:
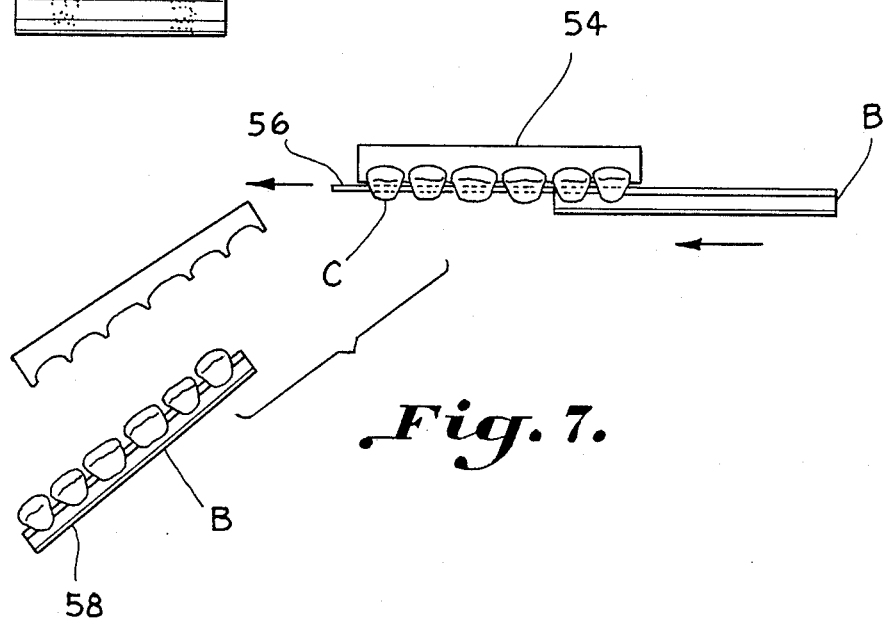
FIG. 7 is a schematic view illustrating a system and method for automatically carding artificial teeth manufactured in accordance with the invention on a tooth card after molding.

Referring now in more detail to FIG. 7, an automatic process and method is schematically illustrated for automatically placing the artificial teeth on tooth cards B after molding in accordance with the invention. It is to be understood that the artificial teeth heretofore described will be made in accordance with conventional molding techniques, preferably injection molding. Since these molding techniques are well known in the art, only so much of the molding process is illustrated as is necessary to an understanding of the invention. In this case, the molded teeth retained on a conventional mold cavity 54 may be automatically loaded on a tooth card B. For this purpose, a molding rod 56 which molds retainer slot 26 into the artificial teeth will be removed in the direction of the arrow shown in FIG. 7 so that a tooth card B may be fed through retainer slot 26 simultaneously carding the teeth on tooth card strip B. Once the card B is loaded with teeth, the loaded card 58 may be delivered for further processing.

An alternate construction and method for the manufacture and carding of artificial teeth is illustrated in FIGS. 9–12. FIG. 9 illustrates an acrylic posterior tooth E having a retainer bar 70 molded or cemented to a tooth back 72. A plastic anterior tooth F may also include such a retainer bar 70 (FIG. 11). A shank 74 of the retainer bar fits in a slit 16 of retainer tube 12 and an enlarged bulbous head 76 prevents lateral movement relative to slit 16. The width of slit 16 may be made such that the prongs tightly grip shank 74 for secure retention by retainer tube 12. The same is true in the case of pins 32 of anterior teeth D. The retainer bar may not be continuous across the tooth back but may be segmented into two or more retainer bars or pins 78 (FIG. 12) having a shank 80 and enlarged bulbous heads 82 formed on plastic anterior tooth F.

In the case of the embodiment of FIGS. 9–12, the same automatic molding and loading of teeth E or F may be accomplished according to FIG. 7. The shanks (74, 80) will slide longitudinally through slit (16) to load retainer tube (12) on card B. Loading of the teeth onto an auxilary holder (not shown) may be necessary before loading onto card B where the teeth must first be removed from a mold sprue.

While a preferred embodiment of the invention has been described using specific terms, such description is for illustrative purposes only, and it is to be understood that changes and variations may be made without departing from the spirit or scope of the following claims.

What is claimed is:

1. A method for carding artificial teeth comprising:
   providing an elongated tooth carding strip having a vertical flange and a retainer tube carried on said vertical flange for retaining a series of said tooth on said card;
   providing said retainer tube in the form of a split retainer tube having a narrow longitudinal slit formed along the length thereof;
   providing artificial teeth having retainer means carried on tooth back thereof; and
   arranging said teeth on said tooth card such that said retainer means of said teeth is engaged by said retainer tube for retention on said tooth card.

2. The method of claim 1 including providing said tooth card in a form having a base divided by said vertical flange defining a first base on one side of said flange and a second base on an opposing side of said flange.

3. The method of claim 2 including providing identification indicia on one of said bases for identifying the type teeth carded on said tooth card.

4. The method of claim 2 including providing indicia on said first base to indicate upper denture teeth and providing indicia on said second base to indicate lower denture teeth.

5. The method of claim 1 wherein said retainer tube is provided in a form having first and second opposed flexing prong-like edges terminating at and created by said slit for allowing said split tube to compress for engagement with said retainer means.

6. The method of claim 5 including providing said retainer means in the form of an elongated retainer slot formed continuously across said tooth being open from said tooth back receivable over said retainer tube for retention of said tooth.

7. The method of claim 5 including providing said retainer means in the form of a retainer bar carried by said tooth back having a shank receivable in said slit of said retainer tube between said first and prong-like edges and an enlarged head receivable in a hollow interior of said retainer tube preventing outward movement thereof.

8. The method of claim 6 including providing said retainer means in the form of a pair of spaced retainer bars each having a shank receivable in said slit of said retainer tube for tight retention by said prong-like edges and an elongated head prevent outward movement thereof.

9. Apparatus for carding and identifying artificial teeth comprising:
   an elongated tooth card having a widened base and a vertical flange extending upwardly from said base;
   a tooth retainer tube carried by said vertical flange including a narrow elongated slit formed along a length of said retainer tube; and
   molded artificial teeth having retainer means formed on a back of said teeth for retention by said retaining tube in such a manner that said teeth may be moved longitudinally on said retainer tube.

10. The system of claim 9 wherein said retainer means comprises a retainer slot formed in said teeth across a tooth back having a cross-section conforming generally to that of the cross-section of said retainer tube so that said artificial teeth may be retained by said retainer tube by insertion over said retainer tube.

11. The apparatus of claim 9 wherein said retainer means comprises a shank affixed to a tooth back of said teeth and an enlarged head carried on the end of said shank in a manner that the shank is received through said slit of said retainer tube and said head is received in a hollow interior of said retainer tube so that relative longitudinal movement between said teeth and retainer tube is permitted while outward movement is prevented.

12. The apparatus of claim 9 wherein said retainer tube includes first and second flexible prong-like edges formed on opposing sides of said slit which flex towards each other to facilitate insertion and removal of said retainer means onto said tooth card.

13. The apparatus of claim 12 wherein said first and second prong-like edges are off set so that they may overlap each other when flexed to insert into said retainer means.

14. The apparatus of claim 12 wherein said retainer means of said artificial teeth may be received over said retainer tube either by sliding longitudinal axial movement or inward movement.

15. A system for carding and identifying artificial teeth for the manufacture of dentures comprising:
   a tooth card for holding a set of artificial teeth;
   said tooth card having a base and a vertical flange extending upwardly from said base defining a first base surface on one side of said flange and a second base surface on the opposing side of said flange;
   a tooth retainer tube carried by said vertical flange generally along the entire length of said tooth card;
   artificial teeth having a retainer means for engagement with said retainer tube in a manner that relative longitudinal movement between said artificial teeth and said retainer tube of said tooth card is facilitated; and
   identification indicia carried by said base of said tooth card identifying said artificial teeth as a prescribed set of teeth.

16. The system of claim 15 wherein said identification indicia includes a first code section carried adjacent one end of said carding strip indicating posterior or anterior teeth and a second code section code section carried adjacent an opposite end of said card indicating upper or lower denture teeth.

17. The system of claim 16 wherein said second code section is carried on said first base surface to indicate upper denture teeth and carried on said second base surface to indicate lower denture teeth.

18. The system of claim 16 wherein said first and second code sections are color coded sections.

19. The system of claim 18 wherein said identification indicia further includes indicia indicating the mold and shade of said artificial teeth imprinted on front of said first and second base surfaces.

20. The system of claim 17 wherein said first code section is carried on both said first and second base surfaces of said tooth card face, and said second code section is carried only on one of said first and second bases.

21. An artificial tooth display device for displaying artificial teeth, comprising:
(a) a longitudinal horizontal base;
(b) a longitudinal flange extending from said base at an angle thereto;
(c) a tooth retainer tube having a longitudinal slit in its wall extending substantially the length of said tube, said tube being disposed along an edge of said flange; and
(d) a plurality of artificial teeth, disposed on said retainer tube each of which has integral means on its back part for slidingly engaging said retainer tube to retain and support said teeth for display purposes.

22. An artificial tooth display device as set forth in claim 21, wherein said integral means comprises a retainer slot formed in said teeth, across a tooth back having a cross-section conforming generally to that of the cross-section of said retainer tube so that said artificial teeth may be retained by said retainer tube by insertion over said retainer tube.

23. An artificial tooth display device as set forth in claim 21, wherein said integral means comprises a shank affixed to a tooth back of said teeth and an enlarged head carried on the end of said shank in a manner that the shank is received through said slit of said retainer tube and said head is received in a hollow interior of said retainer tube so that relative longitudinal movement between said teeth and retainer tube is permitted while outward movement is prevented.

24. An artificial tooth display device as set forth in claim 21, wherein said retainer tube includes first and second flexible prong-like edges formed on opposing sides of said slit which flex towards each other to facilitate insertion and removal of said retainer means onto said tooth card.

25. An artificial tooth display device as set forth in claim 24, wherein said first and second prong-like edges are offset so that they may overlap each other when flexed to insert into said retainer means.

26. An artificial tooth display device as set forth in claim 24, wherein said retainer means of said artificial teeth may be received over said retainer tube either by sliding longitudinal axial movement or inward movement.

* * * * *